(12) United States Patent
Held

(10) Patent No.: US 6,217,511 B1
(45) Date of Patent: Apr. 17, 2001

(54) SURGICAL ENDOSCOPE

(75) Inventor: Manfred Held, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

(21) Appl. No.: 09/269,127
(22) PCT Filed: Jul. 14, 1998
(86) PCT No.: PCT/EP98/04360
  § 371 Date: Mar. 19, 1999
  § 102(e) Date: Mar. 19, 1999
(87) PCT Pub. No.: WO99/09878
  PCT Pub. Date: Mar. 4, 1999

(30) Foreign Application Priority Data

Aug. 23, 1997 (DE) .......................................... 297 15 168 U

(51) Int. Cl.⁷ ............................................................ A61B 1/00
(52) U.S. Cl. ........................... 600/131; 600/106; 600/164
(58) Field of Search ............................... 600/101, 102, 600/105, 106, 131, 164

(56) References Cited

U.S. PATENT DOCUMENTS

| 4,137,920 | * | 2/1979 | Bonnet | 128/311 |
| 4,430,996 | * | 2/1984 | Bonnet | 128/303 |
| 5,014,708 | * | 5/1991 | Hayashi et al. | 128/653 |
| 5,088,998 | * | 2/1992 | Sakashita et al. | 606/46 |
| 5,151,101 | | 9/1992 | Grossi et al. | 606/46 |
| 5,169,397 | * | 12/1992 | Sakashita et al. | 606/27 |
| 5,486,155 | * | 1/1996 | Muller et al. | 600/137 |
| 5,685,853 | * | 11/1997 | Bonnet | 604/164 |
| 5,807,240 | * | 9/1998 | Muller et al. | 600/135 |
| 5,921,916 | * | 7/1999 | Aeikens et al. | 600/108 |

FOREIGN PATENT DOCUMENTS

| 79 13 986 | 8/1979 | (DE) . |
| 34 43 337 | 5/1986 | (DE) . |
| 37 41 879 | 6/1988 | (DE) . |
| 38 03 212 | 8/1989 | (DE) . |
| 39 23 851 | 8/1990 | (DE) . |
| 195 11 092 | 9/1996 | (DE) . |

\* cited by examiner

Primary Examiner—Linda C. M. Dvorak
Assistant Examiner—Jocelyn Ram
(74) Attorney, Agent, or Firm—Rankin, Hill, Porter & Clark LLP

(57) ABSTRACT

A surgical endoscope has a shaft and a main body affixed to the proximal end of the shaft. A duct to permit passage of an operating implement extends through the main body. An optics and a fiber optics extend through the main body from an ocular and/or camera adapter and a fiber optics hookup which are mounted on the main body. A thumb grip having a proximal gripping surface and a first finger-grip having a distal gripping surface are attached to opposite sides of the main body so that the finger gripping surface is distally offset from the thumb gripping surface and is circularly separated from it by substantially 180°.

5 Claims, 1 Drawing Sheet

SURGICAL ENDOSCOPE

FIELD OF THE INVENTION

The invention relates to a surgical endoscope with a shaft and a main body mounted proximally to the shaft, an operative duct for passing a surgical instrument through the body, and optics extending through the endoscope.

BACKGROUND OF THE INVENTION

Endoscopes of this type are held and guided by the surgeon in the fingers of one hand when performing surgery. The fingers seize the endoscope by its main body.

The surgeon must manually move the endoscope in order, for example, to insert it into an aperture in a patient's body. This insertion entails rotating, pivoting, pushing and pulling the endoscope which is furthermore required to exactly follow the surgeon's manual guidance to prevent injury to the patient's tissue or vessels.

As a result, absolutely reliable gripping contact between the fingers of the guiding hand and the endoscope must be assured. The surgeon's other hand holds the proximal end of an operative tool inserted into the endoscope's operative duct and, by driving that tool, performs specific functions at the site of surgery.

Endoscopes of this type are used in particular in the form of ureteroscopes. The surgeon must insert the ureteroscope through the patient's urethra, pass it through the bladder space and then guide the ureteroscope through the ostium into the ureter. The described path is traversed while rotating, pivoting and pushing the ureteroscope. Reliable gripping contact between the fingers of the guiding hand and the ureteroscope must be assured to preclude injuring delicate tissue, for instance the bladder or ureter, by unintended ureteroscope displacements.

Conventional endoscopes incur the substantial drawback of lacking dedicated gripping surfaces. Such endoscopes are seized at arbitrary sites, almost anywhere on the main body which, however, does not allow secure and convenient gripping. Truly safe handling cannot be achieved. Because the main body is seized in a more or less unconstrained manner, there may follow undesired actuation of functional elements such as valves, switches or the like.

SUMMARY OF THE INVENTION

Accordingly, an object of the present invention is to provide an endoscope of the type discussed above which provides for reliable gripping contact between the fingers and the endoscope's main body, thereby securely holding and guiding the endoscope.

The endoscope of the invention is fitted with a thumb-grip and a finger-grip. Accordingly, the endoscope no longer is seized just anywhere on the main body, but rather it is seized at sites dedicated to the thumb and fingers. In this manner, the endoscope may be held conveniently and without fatigue. The invention allows firm gripping in order to also absorb or exert high forces. Because of the reliable finger action on the dedicated gripping surfaces, the danger of erroneous actuations caused by spuriously driving valves, switches or the like is reduced.

In an especially advantageous embodiment, the thumb grip is situated above the endoscope axis, allowing the surgeon to hold the endoscope by a large area. This ergonomic design prevents premature fatigue, for instance, of the surgeon's arm.

In an advantageous manner, providing a second finger grip allows still more reliable gripping of the endoscope. The endoscope is held between the fingers of one hand, for instance, between the index and the middle fingers of one hand and the thumb of the same hand. In other words, the endoscope is held at three points.

In a further embodiment, providing fiber optics extending transversely to the main body, and using the fiber optics as the second finger grip allows saving one component which lowers costs.

In a further advantageous embodiment, an ocular or camera adapter projects obliquely from the main body and the thumb grip is mounted at an acute angle therebetween. An ergonomically advantageous gripping position is secured to prevent the thumb from being wedged into the angle apex.

By situating the thumb grip in the ocular, the instrument insertion along the proximal endoscope axis can be made very short and thereby the endoscope can be made shorter and more easily handled.

BRIEF DESCRIPTION OF THE DRAWINGS

The invention is shown in illustrative and schematic manner in the accompanying drawings in which.

DESCRIPTION OF PREFERRED EMBODIMENTS

Figure 1:
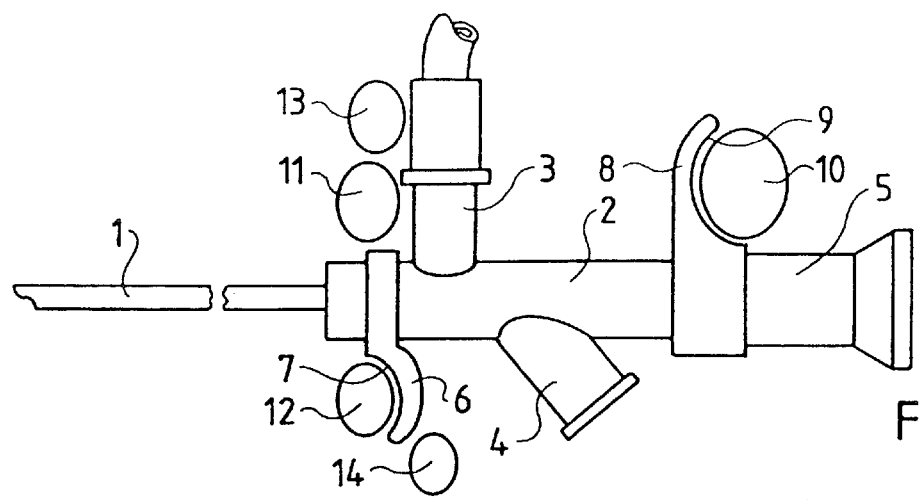
FIG. 1 is a side elevation of a surgical endoscope fitted with a thumb-grip and a finger-grip.

FIG. 1 shows a surgical endoscope consisting distally of a shaft 1 and proximally of a main body 2. Main body 2 is fitted with a fiber optics hookup 3 and an instrument intake stub 4 oblique to main body 2. An ocular 5 at the proximal end of main body 2 may also be used as a camera adapter. This figure also shows a first finger grip 6 with a distal gripping surface 7 and a thumb grip 8 with a proximal gripping surface 9.

The thumb and the finger of the hand guiding the endoscope are shown in highly schematic manner: the endoscope is gripped by the thumb 10, the middle finger 11 and the fourth finger 12. The index finger 13 and the small finger 14 are also indicated. This FIG. clearly shows how the fiber optics hookup 3 also serves as a second finger grip.

Figure 2:
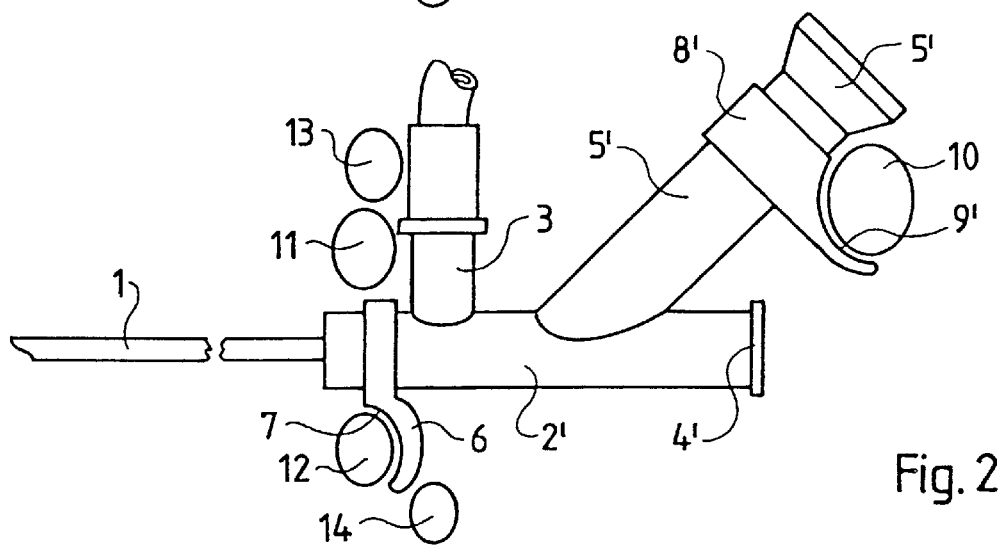
FIG. 2 is a side elevation of a surgical endoscope comprising a laterally oblique ocular fitted with one thumb-grip and one finger-grip.

FIG. 2 shows a surgical endoscope with an ocular 5' oblique to the main body 2' and with a proximal instrument intake stub 4' extending in the axial direction. In this embodiment, thumb grip 8' is mounted on ocular 5'.

Figure 3:
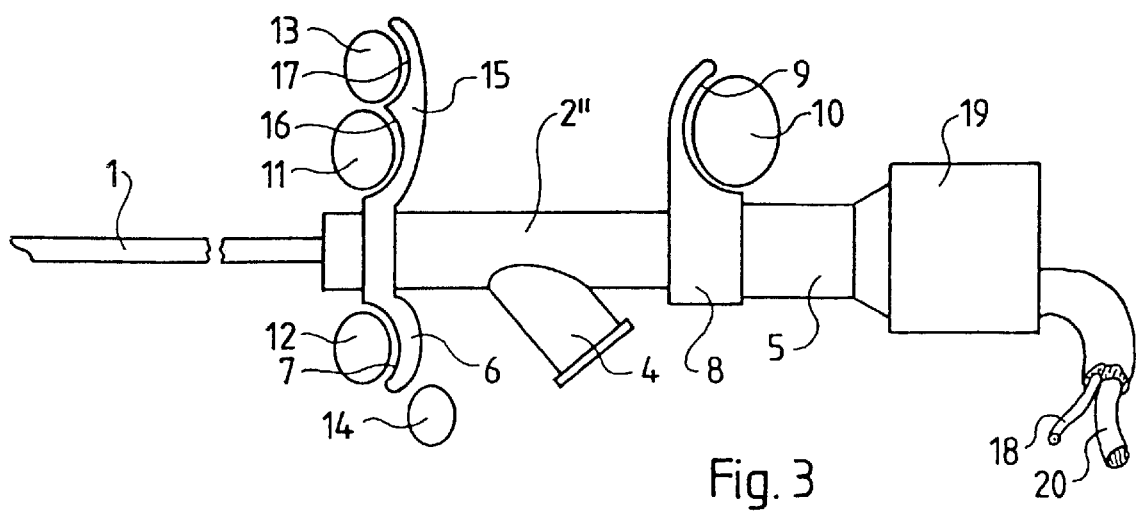
FIG. 3 is a side elevation of a surgical endoscope according to FIG. 1 but with a camera mounted at the proximal end of the main body and a fiber optics adapter at this camera and a bilateral finger-grip.

Lastly, FIG. 3 shows an endoscope without an obliquely projecting fiber optics hookup. It shows a main body 2" on which is affixed a first finger grip 6 together with a second finger grip 15. The two finger grips 6 and 15 are integral with each other in this embodiment. Second finger grip 15 of this embodiment is fitted with two distal gripping surfaces 16 and 17 to hold, in this instance, middle finger 11 and index finger 13. Fourth finger 12 acts on gripping surface 7 of first finger grip 6. In this design, also, reliable gripping is assured by three gripping surfaces.

In this embodiment, fiber optics 18 is connected to a camera 19 proximally mounted on ocular 5. A camera cable 20 is also shown.

The two finger grips 6 and 15 also may be mounted in a slight variation from the shown 180° position. Furthermore, thumb grip 8 and finger grip 6 of FIG. 1 may be mounted at an angle somewhat different from the one of 180° shown therein.

The manner shown in the above Figures in which the endoscope is held with the fingers, namely between the middle and fourth fingers, also can be varied. Illustratively the endoscope may be held between the index and the middle fingers.

Other designs also are conceivable. For instance, thumb grip 8' of FIG. 2 may be mounted in clamped manner between ocular 5' and main body 2' or between the ocular 5' and instrument insertion stub 4'.

The finger grips also may be designed for all four fingers of one hand and correspondingly be fitted with four distal gripping surfaces. The grips may also be closed on themselves to constitute finger and/or thumb rings.

Additionally, the grips may be designed in a manner to allow retrofitting conventional endoscopes with them, for instance in the form of plug-on plastic molded parts. Also all grips may be combined into one component which then is joined as one unit to the endoscope.

What is claimed is:

1. A surgical endoscope comprising:

a shaft;

a main body mounted proximally to said shaft;

an operative duct for passing a surgical instrument through said body;

optics and fiber optics extending from an ocular and/or a camera adapter and a fiber optics hookup mounted on the main body and extending through the endoscope, said fiber optics hookup being disposed on a first side of the main body;

a thumb grip (8) having a proximal gripping surface (9), said thumb grip being located on said first side of the main body; and a first finger-grip (6) with a distal gripping surface (7) mounted on said main body (2,2"), said first finger grip (6) being circularly offset from said thumb grip (8) by substantially 180°.

2. An endoscope according to claim 1 including a second finger-grip (15) having a distal gripping surface (16, 17) mounted substantially in the same axial position as said first finger-grip (6) and being circularly spaced substantially 180° from said first finger grip.

3. A surgical endoscope comprising:

a shaft;

a main body mounted proximally to said shaft;

an operative duct for passing a surgical instrument through said body;

optics and fiber optics extending from an ocular and/or a camera adapter and a fiber optics hookup mounted on the main body and extending through the endoscope;

a thumb grip (8) having a proximal gripping surface (9);

a first finger-grip (6) with a distal gripping surface (7) mounted on said main body (2,2"), said first finger grip (6) being circularly offset from said thumb grip (8) by substantially 180°;

a second finger-grip (15) having a distal gripping surface (16, 17) mounted substantially in the same axial position as said first finger-grip (6) and being circularly spaced substantially 180° from said first finger grip; and, a fiber optics hookup substantially extending transversely to the main body wherein said fiber optics hookup (3) also forms said second finger grip.

4. A surgical endoscope comprising:

a shaft;

a main body mounted proximally to said shaft;

an operative duct for passing a surgical instrument through said body;

optics and fiber optics extending form an ocular and/or a camera adapter and a fiber optics hookup mounted on the main body and extending through the endoscope;

a thumb grip (8) having a proximal gripping surface (9); and a first finger-grip (6) with a distal gripping surface (7) mounted on said main body (2,2"), said first finger grip (6) being circularly offset from said thumb grip (8) by substantially 180°; and, an ocular and/or camera adapter projecting obliquely from the main body, said thumb grip (8') being mounted at an acute angle between said ocular or camera adapter (5'), and said main body (2').

5. An endoscope according to claim 4 wherein said thumb grip (8') is located on said ocular (5').

* * * * *

UNITED STATES PATENT AND TRADEMARK OFFICE
CERTIFICATE OF CORRECTION

PATENT NO. : 6,217,511 B1
DATED : April 17, 2001
INVENTOR(S) : Held

It is certified that error appears in the above-identified patent and that said Letters Patent is hereby corrected as shown below:

Title page,
Item [54], delete "SURGICAL ENDOSCOPE" and insert -- SURGICAL ENDOSCOPE WITH FINGER GRIP --.

Column 1,
Line 1, delete "SURGICAL ENDOSCOPE" and insert -- SURGICAL ENDOSCOPE WITH FINGER GRIP --.

Signed and Sealed this

Thirtieth Day of October, 2001

Attest:

NICHOLAS P. GODICI
Attesting Officer    Acting Director of the United States Patent and Trademark Office

(12) EX PARTE REEXAMINATION CERTIFICATE (7041st)
United States Patent
Held

(10) Number: US 6,217,511 C1
(45) Certificate Issued: Sep. 1, 2009

(54) SURGICAL ENDOSCOPE WITH FINGER GRIP

(75) Inventor: Manfred Held, Hamburg (DE)

(73) Assignee: Olympus Winter & IBE GmbH, Hamburg (DE)

Reexamination Request:
No. 90/010,213, Jul. 1, 2008

Reexamination Certificate for:
Patent No.: 6,217,511
Issued: Apr. 17, 2001
Appl. No.: 09/269,127
Filed: Mar. 19, 1999

Certificate of Correction issued Oct. 30, 2001.

(22) PCT Filed: Jul. 14, 1998

(86) PCT No.: PCT/EP98/04360
§ 371 (c)(1),
(2), (4) Date: Mar. 19, 1999

(87) PCT Pub. No.: WO99/09878
PCT Pub. Date: Mar. 4, 1999

(30) Foreign Application Priority Data
Aug. 23, 1997 (DE) ..................... 297 15 168 U

(51) Int. Cl.
*A61B 1/04* (2006.01)
*A61B 1/00* (2006.01)
*G02B 23/24* (2006.01)

(52) U.S. Cl. .......... 600/131; 600/106; 600/164
(58) Field of Classification Search ............ None
See application file for complete search history.

(56) References Cited

U.S. PATENT DOCUMENTS

| | | |
|---|---|---|
| 4,027,510 A | 6/1977 | Hiltebrandt |
| 4,372,295 A | 2/1983 | Heckele |
| 4,620,547 A | 11/1986 | Boebel |
| 5,088,998 A | 2/1992 | Sakashita et al. |
| 5,170,774 A | 12/1992 | Heckele |
| 6,217,511 B1 | 4/2001 | Held |

FOREIGN PATENT DOCUMENTS

DE     79 13 986     8/1979

*Primary Examiner*—David O. Reip

(57) ABSTRACT

A surgical endoscope has a shaft and a main body affixed to the proximal end of the shaft. A duct to permit passage of an operating implement extends through the main body. An optics and a fiber optics extend through the main body from an ocular and/or camera adapter and a fiber optics hookup which are mounted on the main body. A thumb grip having a proximal gripping surface and a first finger-grip having a distal gripping surface are attached to opposite sides of the main body so that the finger gripping surface is distally offset from the thumb gripping surface and is circularly separated from it by substantially 180°.

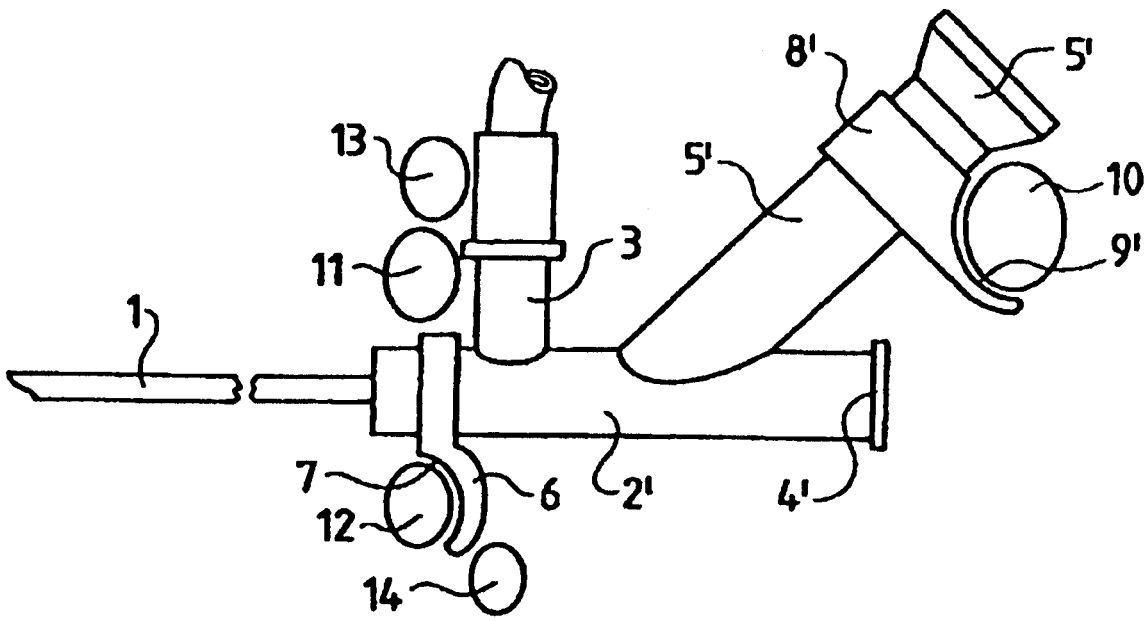

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 2 is confirmed.

Claims 3–5 were not reexamined.

\* \* \* \* \*